United States Patent [19]

LaConti

[11] 4,025,412
[45] May 24, 1977

[54] ELECTRICALLY BIASED TWO ELECTRODE, ELECTROCHEMICAL GAS SENSOR WITH A $H_2$ COUNTER/REFERENCE ELECTRODE INCORPORATING A HYDROGEN STORAGE BUFFERING SYSTEM

[75] Inventor: Anthony B. LaConti, Lynnfield, Mass.

[73] Assignee: General Electric Company, Wilmington, Mass.

[22] Filed: Dec. 4, 1975

[21] Appl. No.: 637,518

[52] U.S. Cl. .................................. 204/195 R
[51] Int. Cl.$^2$ ........................... G01N 27/52
[58] Field of Search ............... 204/1 K, 1 N, 195 R, 204/1 T; 23/232 E, 254 E

[56] References Cited
UNITED STATES PATENTS

| | | | |
|---|---|---|---|
| 3,149,921 | 9/1964 | Warner | 23/232 |
| 3,776,832 | 12/1973 | Oswin et al. | 204/195 R |
| 3,824,166 | 7/1974 | Deibert | 204/195 R |
| 3,835,013 | 9/1974 | Grubb et al. | 204/195 P |

*Primary Examiner* — G. L. Kaplan

[57] ABSTRACT

The instant invention relates to an electrochemical sensor for detecting gases or vapors such as carbon monoxide, alcohol NOX etc. The gas sensor includes either a solid polymer ion-exchange-membrane electrolyte or a liquid electrolyte adsorbed in a suitable matrix, a catalytic sensor electrode and a combination counter/reference electrode.

A biasing voltage is applied between the electrodes. The biasing voltage is made equal to or larger than the oxidation/reduction potential of a platinum/air electrode and is also greater than the reversible oxidation/reduction potential of the gas or vapor to be detected. As a result, the gas or vapor to be detected is rapidly oxidized at the sensor electrode to produce a current proportional to the mass of the gas present in the incoming stream, while at the same time, making the device insensitive to air. The counter/reference electrode is of a novel construction to provide optimum reversible hydrogen evolution and a hydrogen buffering or storage arrangement to maintain the reference electrode potential substantially constant at 0.0 volts. The electrode is fabricated of a noble metal alloy. Associated with the electrode is a perforated foil such as palladium which has a high solubility for hydrogen. The molecular hydrogen produced at the counter/reference electrode is absorbed in the palladium. An invariant hydrogen atmosphere is thus maintained at the counter/reference electrode so that the reference electrode voltage is kept substantially at zero volts.

9 Claims, 6 Drawing Figures

ELECTRICALLY BIASED TWO ELECTRODE, ELECTROCHEMICAL GAS SENSOR WITH A $H_2$ COUNTER/REFERENCE ELECTRODE INCORPORATING A HYDROGEN STORAGE BUFFERING SYSTEM

The instant invention relates to an electrochemical gas or vapor sensor, and more particularly, to an electrochemical sensor for detecting gases or vapors such as carbon monoxide, alcohol etc. The sensor is a two electrode device which has low power consumption, is small, light in weight, simple in construction, has a minimum amount of external electrical circuitry and may therefore be utilized as a portable device for detecting gases or vapors.

The use of electrochemical cells to detect various gaseous constituents such as hydrogen, oxygen, carbon monoxide etc. has been described in various publications and patents. An electrochemical sensor may be defined as a gas sensor in which the gaseous constituents to be detected is passed by a catalytic electrode so that the constituent is either oxidized or reduced with the exchange of electrons. The flow of current due to the oxidation and reduction of the gaseous constituent is then a measure of the concentration of the constituent to be detected. One early form of such an electrochemical gas detection device for detecting hydrogen and oxygen is described in U.S. Pat. No. 3,149,921, Warner — Method of Measuring the Partial Pressure of a GAs, issued Sept. 22, 1964 and assigned to the General Electric Company, the assignee of the present invention. In the Warner patent, a modified fuel cell structure is used as a gas sensor. The cell includes a solid polymer electrolyte and two catalytic electrodes. A fuel gas and a reducing gas are respectively supplied to the electrodesas they would be in a fuel cell. In the Warner cell, the gas to be detected (as for example, oxygen) is supplied at less than the stiochiometric ratio at which hydrogen and oxygen are consumed to generte electricity. Consequently, as the amount of oxygen in the one stream varies, the amount of current flow and the voltage generated by the cell varies and is a measure of the concentration of the oxygen. In order for the Warner detector to function properly, gases such as hydrogen or oxygen must be furnished to cell. This obviously requires, in the case of oxygen detection, that a source of hydrogen such as bottled hydrogen be made available for the cell to function properly. This requirement for an independent supply of one of the gases presents difficulties in that it increases the size, bulk and weight of the device and for all practical purposes excludes its use as a portable device. Thus, the fuel cell type of electrochemical gas detector has limitations which can restrict the applicability of the device. This is certainly so in applications such as detection of alcohol on the breath where in situ testing is desirable or in those cases, such as the detection of carbon monoxide or other noxious gases where it is desirable that the sensor be portable so that it may be easily carried or worn by an individual.

Another type of electrochemical gas detector for gases such as hydrogen, carbon monoxide, hydrocarbons, etc. is described in an article entitled, "Electrochemical Detection of $H_2$, CO and Hydrocarbons in Inert or Oxygen Atmospheres" by AB LaConti and HJR Maget printed in the Journal of Electrochemical Society, Vol. 118, No. 3, March 1971. The electrochemical gas detector described in this article is a two-electrode device in which an electrical biasing potential is applied across the electrodes in such a manner that the sensing electrode potential is maintained at a voltage at which the gaseous constituent to be detected is immediately oxidized even in the presence of oxygen at the electrode surfaces. As a result, gases such as hydrogen, carbon monoxide and hydrocarbons may be easily detected in oxygen containing atmospheres. Furthermore, by virtue of the electrical biasing, the rest potential of hydrogen/oxygen acid fuel cell is exactly countered so that no current flows in an external circuit absent the constituent to be detected. By virtue of this electrical biasing arrangement, the power consumption of the device can be reduced substantially in that the cell consumes virtually no power during those intervals when no detectable gases are present. The electrochemical sensor described in the LaConti/Maget article, while a substantial improvement over the type of detectors shown in the Warner patent still has certain shortcomings which also limited its usefulness and utility. Even with electrical biasing, it is still necessary, in order to maintain the reference/counter electrode at a constant potential (i.e., at the $Pt/H_2$ electrode potential of zero volts) to provide a source of hydrogen for the counter/reference electrocde. If hydrogen is not present at the reference electrode, the reference electrode voltage has a tendency to drift. As a result, the differential voltage across the electrodes shifts so that the sensing electrode is no longer at the desired rest potential and the rate at which oxidation or reduction takes place varies. This can introduce errors into the detection process. Thus, the electrically biased electrochemical sensor described by LaConti and Maget also required a separate source of hydrobgen in order to operate properly. As pointed out previously, the requirement for such a separate source of hydrogen, bottled or otherwise, is a serious limitation on the application of the gas detector under certain circumstances.

Another existing electrochemical gas sensor which eliminates the need for bottled or other sources of hydrogen for the reference electrode, is described in a U.S. Pat. No. 3,776,832 issued Dec. 4, 1973 entitled "Electrochemical Detection Cell" and in an article entitled "Controlled Potential Electrochemical Analysis of Carbon Monoxide" found in the 1974 issue of American Laboratory on pages 50 et seq. The device described in these two publications is a three electrode electrochemical cell, i.e., the cell contains a sensing electrode, a counter electrode and a reference electrode. A potentiostat is coupled between the reference and the sensing electrodes to maintain the potential at the sensing electrodes constant with variations in the ambient or environment. This electrochemical gas sensor thus maintains a constant voltage at the reference electrode without the need for a source of hydrogen. This scheme avoids the problems associated with providing a separate source of hydrogen, but in doing so, introduce other difficulties. This is, the potentiostatic circuitry requires a substantial number of electrical components external to the cell, and requires an extra electrode within the cell. This adds to the complexity of the cell itself and by virtue of the circuitry associated therewith, increases the complexity, size, and cost of the device, while at the same time, introducing maintenance and reliability problems as the number of components increases.

Consequently, there is a need for an electrochemical gas sensor which is simple in construction, has good sensitivity, does not, on the one hand, require a separate source of gas such as hydrogen for the reference electrode, and, on the other hand, does not require elaborate electrical circuitry to maintain the potential at the sensing electrode current.

It is therefore a primary objective of this invention to provide a two-electrode electrochemical gas sensor having a self-contained hydrogen counter/reference electrode which does not require an independent supply of hydrogen gas.

It is another objective of this invention to provide an electrically biased two-electrode, electrochemical gas sensor in which the hydrogen for maintaining the hydrogen reference electrode at a constant voltage is generated directly within the electrochemical sensor.

Yet anotherobjective of the invention is to provide an electrically biased two-electrode gas sensor in which the hydrogen is generated within the cell and is stored in a buffering construction adjacent to the reference/counter electrode to maintain the reference electrode voltage constant.

Yet another objective of the invention is to provide an electrochemical gas sensor which is low in cost, is highly sensitive, is small and portable in nature.

Other objectives and advantages of the invention will become apparent as the description thereof proceeds.

The various objects and advantages of the invention are embodied in an electrochemical gas sensor comprising an electrolyte which may be either of the solid polymer type or the aqueous type absorbed in a matrix, positioned between a pair of catalytic electrides. One catalytic electrode is exposed to a gaseous stream containing constituent which is to be detected while the other electrode, whichis the counter/reference electrode is enclosed in a sealed chamber. A source of electrical biasing potential is connected between the two electrodes and has a magnitude and a polarity such that the potential of the electrode exposed to the gaseous stream, i.e., the sensing electrode, is maintained at a potential equal to or greater than the potential required for rapid oxidation of the gas constituent to be detected. Furthermore, the sensing electrode potential is such that any oxygen in the gaseous stream does not affect the output. That is, the sensing electrode potential is such that the oxygen in the gas stream cannot be reduced and hence does not affect the current flow and the sensor indication. The electrode in the sealed chamber which is the reference/counter electrode has a hydrogen storage element associated therewith to maintain an essentially invariant atmosphere at the reference electrode. As a result, the electrode is maintained at the desired constant potential of 0.0 volts for a $Pt/H_2$ reference electrode. The structure for providing hydrogen storage or buffering preferably takes the form of a foil of material, such as palladium, which has a high solubility for hydrogen, and which is also perforated to increase the surface area and provide additional absorption of the hydrogen. With electrical biasing applied to the electrodes, a humidified incoming gas stream produces sufficient initial dissociation of the water to produce hydrogen ions. The ions are transported through the electrolyte to the counter/reference electrode and are reduced to form molecular hydrogen which is then absorbed in the palladium and stored there to maintain an essentially constant hydrogen partial pressure at the electrode thereby maintaining a constant potential for the $Pt/H_2$ electrode.

The novel features which are believed to be characteristic of this invention are set forth with particularity in the appended claims. The invention itself, however, both as to its organization and mode of operation, together with further objectives and advantages, may best be understood by reference to the following description taken in connection with the accompanying drawings in which:

Figure 1:
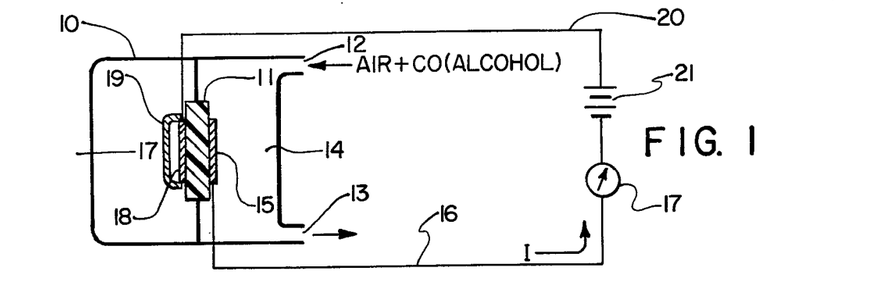
FIG. 1 is a schematic representation of the novel electrically biased gas sensor.

FIG. 1 shows a shematic illustration of an electrochemical gas detecting cell embodying the invention in which a housing 10 is divided into two chambers by an electrolyte containing element 11 which may be either an ion-exchange-membrane such as a perflourocarbon membrane sold by duPont under its trade name "Nafion" or a fiberglas matrix containing an aqueous solution of an acid such as phosphoric acid. An inlet port 12 and an outlet port 13 communicate with a sensing chamber 14 through which a gaseous stream is passed. The gaseous stream which contains the constituent to be detected is brought into contact with a catalytic electrode 15 positioned adjacent to the electrolyte 11. Electrode 15 constitutes the sensing electrode of the detector at which the constituent to be detected such as CO is oxidized. The current which is produced by the electrochemical conversion of the constituent flows through lead 16 to a current measuring instrument 17 to provide an indication or measure of the concentration of the constituent to be detected.

A seal chamber 17 includes a counter/reference electrode 18 positioned closely adjacent to electrolyte 11. A hydrogen storing or "buffering" element 19 is positioned adjacent to electrode 18 and takes the form of a hydrogen absorbing metallic foil. In a preferred embodiment, a perforated palladium foil is used as the buffering element since hydrogen is highly soluble in palladium. By perforating the palladium foil, the total surface exposed to hydrogen is increased thereby increasing the amount of hydrogen absorbed. As a result, hydrogen is stored in the foil to maintain a hydrogen atmosphere at electrode 18. Since chamber 17 is sealed and air is essentially excluded, a hydrogen atmosphere at a substantially constant partial pressure is maintained at electrode 18 and this, in turn, insures that the potential at the electrode is that of a $Pt/H_2$ reference. A lead 20 is connected between counter/reference electrode 18 and the positive terminal of a source of constant unidirectional voltage 21 which may either be a battery, as shown, or constant voltage feedback source. The negative terminal of the voltge source is connected through measuring instrument 17 to the sensing electrode. As was pointed out briefly above, the voltage of battery or constant voltage source 21 is selected so that sensing electrode 15 is maintained at a potential equal or higher than the standard oxidation/reduction potential for the $O_2$ $_:H^+:H_2$) couple so that the $O_2$ in the gas stream has no effect on the sensor. The potential is also sufficiently greater than the oxidation potention of the gaseous constituent to be detected so that the incoming constituent is oxidized rapidly upon contact with the sensing electrode.

The operation of the cell for the detection of a gaseous constituent such as carbon monoxide, for example, is generally as follows:

When the cell is first placed into operation by the closure of a suitable switch, not shown, to connect the biasing voltage to the electrode there is an initial surge of current as a humidified gas stream is brought into sensing chamber 14 through inlet conduit 12. This current surge occurs because some of the water vapor in the stream is dissociated at the sensing electrode in accordance with the reaction:

$$2H_2O \rightarrow 4H^+ + 4e + O_2$$

Because, as pointed out previously, the sensing electrode potential is greater than the oxidation/reduction potential for the $O_2$ $H^+/H_2O$ couple. This electrolysis of some of the water produces hydrogen ions and liberates electrons. The hydrogen ions are transported across the acidic electrolyte to counter/reference electrode 18. Even though chamber 17 is sealed when the unit is originally assembled, some air is trapped in the chamber and as a result, the hydrogen ions react with the oxygen in the air in the chamber to form water according to the reaction:

$$4H^+ + O_2 + 4e = 2H_2O$$

This draws a fairly substantial current and as a result, until the oxygen in chamber 17 is depleted, there is an initial surge of current. Within minutes, however, the oxygen is depleted and the current reaches a low background value (10 to 15 microamps/per centimeter$^2$ of electrode surface). This background current is possibly due to the following reactions:

$$2H_2O \rightarrow 4H^+ + O_x + 4e \text{ (at the sensing electrode)}$$

$$4H^+ + 4e \rightarrow 2H_2 \text{ (at the counter/reference electrode)}$$

That is, even after all the oxygen is depleted in the sealed reference/counter electrode compartment, some water continues to be dissociated at the sensor electrode. The hydrogen ions, migrate across the electrolyte to the counter/reference electrodeand are reduced there to form molecular hydrogen which is dissolved in the palladium foil. Thus, there is a continuous replenishment of hydrogen at the counter/reference electrode to maintain the voltage relatively invariant. Since the number of hydrogen ions thus produced is small, the background current is extremely low in the order of 10 to 15 microamps.

If a gas stream containing carbon monoxide, for example, is brought into the sensing chamber, the rest potential of the sensor electrode which is at about +1.3 volts is substantially higher than the theoretical reduction/oxidation carbon monoxide is oxidized very rapidly and the following reactions occur:

| Electrode | Atmosphere | Electrode Reaction |
|---|---|---|
| Sensing (Pt/Air) | Some CO in air stream | $CO+H_2O=2H^++CO_2+2e$ |
| Counter/reference | Pure $H_2$ | $2H^++2e H_2$ |

-continued

| Electrode | Atmosphere | Electrode Reaction |
|---|---|---|
| (Pt/H$_2$) | | |

It can be seen that as the carbon monoxide is oxidized to carbon dioxide and the water is dissociated, electrons are released which flow in the external circuit and hydrogen ions are transported through the electrolyte to the counter electrode and are reduced to form molecular hydrogen. The current flowing in the external circuit is thus directly proportional to the quantity of carbon monoxide present in the air stream.

Since the potential on the sensing electrode is maintained at a level which is substantially greater in the oxidizing direction than the potential required to oxidize carbon monoxide, the carbon monoxide is oxidized rapidly and completely at the sensing electrode. That is, the oxidation/reduction potential for $CO/CO_2$ couple is −0.12 volts. Since the voltage at the sensing electrode is at 1.3 volts, (i.e., greater than the required voltage for the $O_2$, $H^+/H_2O$ couple), and is thus even more in the oxidation direction than the standard potential for the $CO/CO_2$ couple, it will be seen that carbon monoxide is oxidized very rapidly at the electrode.

By maintaining this sensing electrode potential constant relative to a hydrogen reference electrode, the rate at which carbon monoxide is oxidized remains constant. This eliminates errors due to variations in the rate of oxidation. Applicant's novel reference/counter electrode with a hydrogen storage or buffering meansprovides an effective vehicle for maintaining the hydrogen atmosphere at a constant partial pressure. In the absence of a storage element and a means for producing additional hydrogen there would be some loss of hydrogen through diffusion, leakage, etc. The partial pressure of the hydrogen at the electrode would therefore change with time and this in turn, varies the potential at the $Pt/H_2$ reference electrode, because the premise of the constant $Pt/H_2$ reference electrode is that a constant partial pressure of hydrogen is maintained at the electrode. Hence, if the partial pressure of the hydrogen at the $Pt/H_2$ electrode changes, the reference potential also changes and no longer remains at 0.0 volts. If the reference potential shifts, the voltage at the sensing electrode which is, for example, 1.3 volts (the value of the constant voltage source or battery) above the reference voltage, changes correspondingly. For example, if the potential at the $Pt/H_2$ reference electrode drops from 0 volts to −0.05 volts, due to a change in hydrogen partial pressure, the sensing electrode which was previously at 1.3 volts is now at 1.25 volts and will oxidize less carbon monoxide. At the high anodic voltages, i.e., 1.3V, the electrochemical reaction is much faster than the purely chemical reaction $2CO + O_2 \rightarrow 2CO_2$.

However, as the potential at the sensor electrode drops due to changes in the potential at $Pt/H_2$ reference electrode, the rate of electrochemical oxidation reactio slows and begins to approach the rate at which the chemical reaction takes place. Consequently, some of the carbon monoxide is converted to $CO_2$ by the chemical reaction rather than by the electrochemical reaction. Since the conversion of carbon monoxide to $CO_2$ by a chemical reaction does not result in transport of $H^+$ ions from anode to cathode, there is no current flow which represents the CO thus converted and the CO concentration indicated by the instrument will be low. By maintaining the voltage at the sensing electrode fixed, this source of error is eliminated. By means of the arrangement as set forth, i.e., the generation of hydrogen at the counter/reference electrode and the storage or "buffering" means for the hydrogen in the form of a foil, such as palladium, having a high solubiity for hydrogen, the hydrogen atmosphere at the reference electrode is maintained at a relativelyconstant partial pressure, thereby concurrently, maintaining the reference electrode potential substantially constant.

Figures 2, 3:
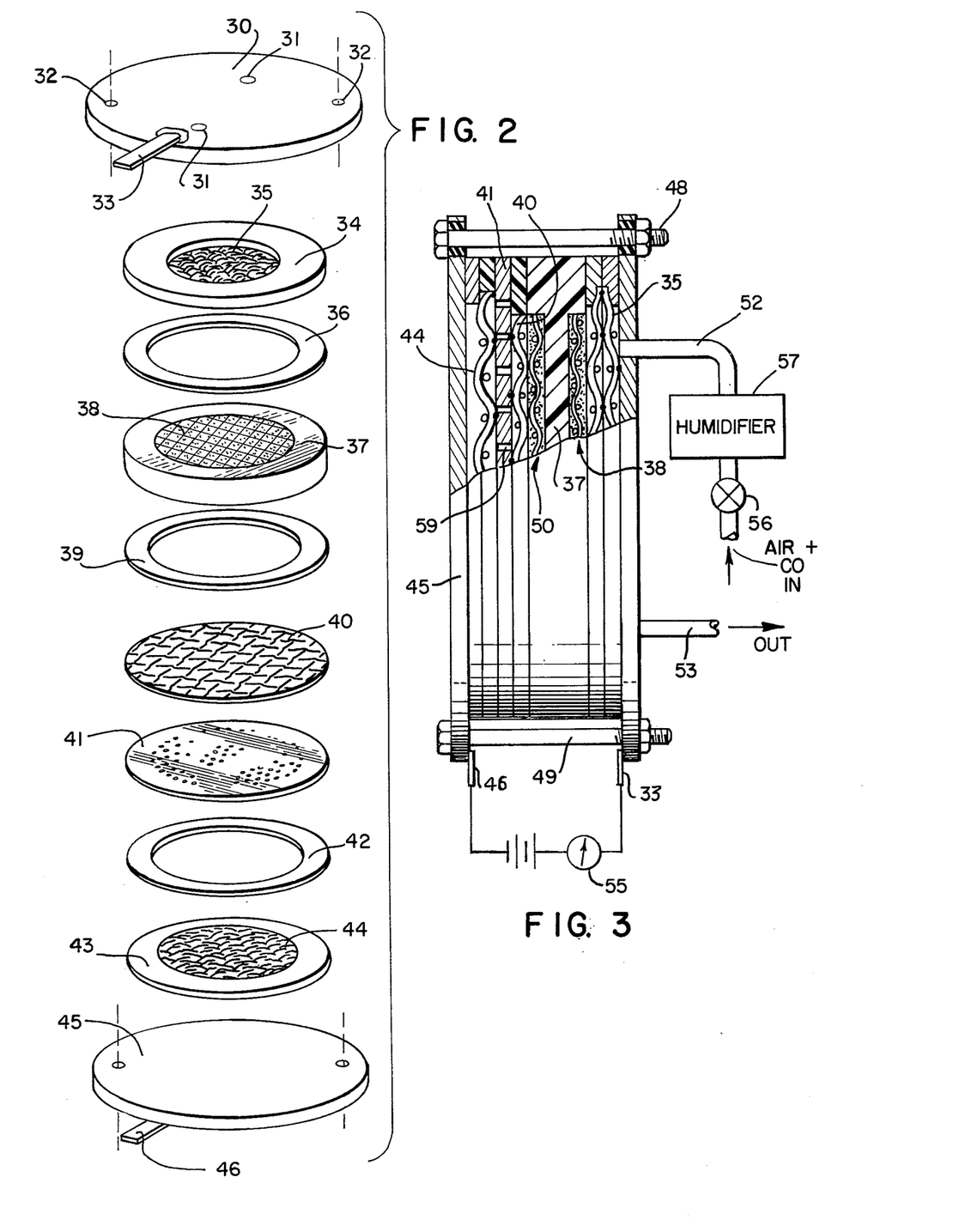
FIG. 2 is an exploded perspective view of the components of a cell assembly of the type having a solid polymer electrolyte.
FIG. 3 is a partial sectional view of the cell in the assembled state.

FIG. 2 is an exploded perspective of an electrochemical gas sensor construction, showing the various components of the cell and their relative spatial orientation. Starting at the top of the FIG. 2 there is a circular titanium endplate 30 having inlet and outlet ports 31 and through which the gas stream containing the gaseous constituents to be measured is brought into and out of the sensing chamber by a pumping arrangement, not shown, but presently to be described. A pair of bolts, not shown, pass through mounting holes 32 in endplate 30 to hold the cell components in the assembled state. A metallic tab 33 is welded or otherwiseattached to the endplate to provide a means for connecting the endplate to a source of DC voltage. Endplate 30 thus acts as a bipolar current collector to allow current flow between the sensor and counter/reference electrodes of the gas detector. A niobium ring collector 34 has a plurality of expanded tantalum or other metallic screens 35 welded to the underside thereof and is positioned tightly against the endplate. The ring and screens provide a conductive path for the current while the welded screen element 35 also provide a means for distributing the incoming gas evenly over the sensor electrode. A sealing gasket ring 36, which is covered on both sides by an adhesive and is made of a flourocarbon such as polytetraflouroethylene which is sold by duPont under its trand designation "Teflon" is positonedbetween niobium ring collector 34 and a solid polymer ion-exchange-membrane electrolyte 37. A catalytic sensor electrode 38 in the form of a reduced platinum and 5% iridium catalyst along with a suitable metallic collector screen is pressed into the surface of the solid polymer electrolyte. Solid polymer electrolyte 37 is a solid sheet of perflourinated sulfonic acid polymer having chemically bound sulfonic acid groups to the backbone. Ionic conductivity is provided by the mobility of hydrogen ions through the polymer passing from sulfonic acid group to group. One form of such a solid polymer electrolyte ion-exchange-membrane is sold by the duPont Company under its trade designation "Naflon." While the perflourinated sulfonic acid polymer is a preferred electrolyte, other solid polymer ion-exchange materials may be utilized with equal facility. A second catalytic electrode, not shown in FIG. 2, is pressed into the underside of the solid polymer electrolyte and constitutes a counter/reference electrode. An adhesive covered sealing gasket ring 39 identical to sealing ring 36 is positioned on the lower side of the solid polymer electrolyte and provides sealing between the electrolyte and a further expanded tantalum gas distribution screen 40.

A perforated, hydrogen storing palladium foil 41 is positioned between screen 40 and a further sealing gasket ring 42. Sealing ring 42 is also covered by an adhesive on both sides to produce a gas tight seal between the perforated hydrogen storing foil and a niobium ring collector 43 having a plurality of welded expanded tantalum screens 44 secured thereto. Sealing gasket 42 and metal screen ring 43 are positioned in physical contact with a second titanium endplate 45 to produce a sealed, gas tight chamber between the palladium foil and endplate 45. A current conductive path is provided from the counter/reference electrode through welded screen 40, perforated plate 41. niobium collector ring 43, screen 44 and endplate 45 which again has a suitable metallic current collector tab 46 attached to the endplate by welding or otherwise.

As may be seen most clerly in FIG. 3, which shows the gas detecting cell of FIG. 2 in the assembled state, the two current collecting endplates 30 and 45 are held together tightly by inslated bolts 48 and 49 passing through the suitable bolt holes in the endplates. Thus, sensingelectrode 38 and a counter/reference electrode 50 are pressed into opposite surfaces of the ion-exchange-membrane 37. The catalytic electrodes are formed of a suitable metallic collector screen and a "Teflon" bonded catalytic electrode supported by the collector screen. The preferred catalyst is a reduced platinum/5% iridiumm alloy which may, if desired, be boned with hydrophobic particles such as polytetraflourethylene. The manner in which such a gas permeable, hydrophobic electrode structure may be fabricated and pressed into the surface of the membrane is illustrated and described in U.S. Pat. No. 3,297,484, Niedrach, et al, issued Mar. 11, 1969 entitled, "Electrode Structure and Fuel Cell Incorporating the same," assigned to the General Electric Company, the assignee of the present invention.

The sensing chamber of the cell, positioned to the right of sensing electrode 38 and the solid polymer electrolyte, incudes the expanded tantalum screens 35 for suitably distributing gas brought into the chamber through input conduit 52. The expanded screens are positioned against sensing electrode 38 and are spot welded together and to endplate 30 to produce a current conducting path between the sensing electrode 38 and the endplate. Electron current produced by the generation of hydrogen ions flows to the endplate and through the tabs 33 and 46 to the other endplate. The current flow which is sensed in a suitable measuring instrument 55 connected in series with the DC battery or other constant voltage source connected across the cell provides a measure of the gas concentration. The incoming stream which includes a gas or vapor constituent which is to be detected, such as carbon monoxide, for example, is brought into the sensing chamber through a valve and pump arrangement 56, and humidifier 57. The humidifier brings the gas stream to a 100% relative humidity prior to introduction into the sensing chamber. Humidification of the gas is necessary in order to supply the water which is dissociated at the sensing electrode to produce the hydrogen ions which are transported across the ion-exchange-membrane to the counter/reference electrode. A preferred method of humidification is to pass the incoming gas over the surface of a solid polymer electrolyte having its other surface flooded with water.

The palladium foil 41 is positioned adjacent to counter/reference electrode 50 but is separated therefrom by screen 40. Foil 41 includes a plurality of holes or perforations, shown in somewhat exaggerated size at 59 to increase the palladium surface area. As a result, hydrogen produced at the counter/reference electrode is stored in sufficient quantity to maintain a substantially invariant hydrogen partial pressure in the vicinity of electrode 50. As a result, a substantially constant Pt/H$_2$ reference potential is maintained and a stable counter/reference electrode is provided.

The chamber to the left of the ion-exchange-membrane 37 consists of the screen element 40, palladium foil 41, conductingscreen 44 and endplate 45. The hydrogen chamber is a closed chamber and contains only the air initially contained therein when the cell is assembled. The oxygen in the air is eventually consumed and replaced by the hydrogen generated at the counter/reference electrode.

Figures 4, 5:
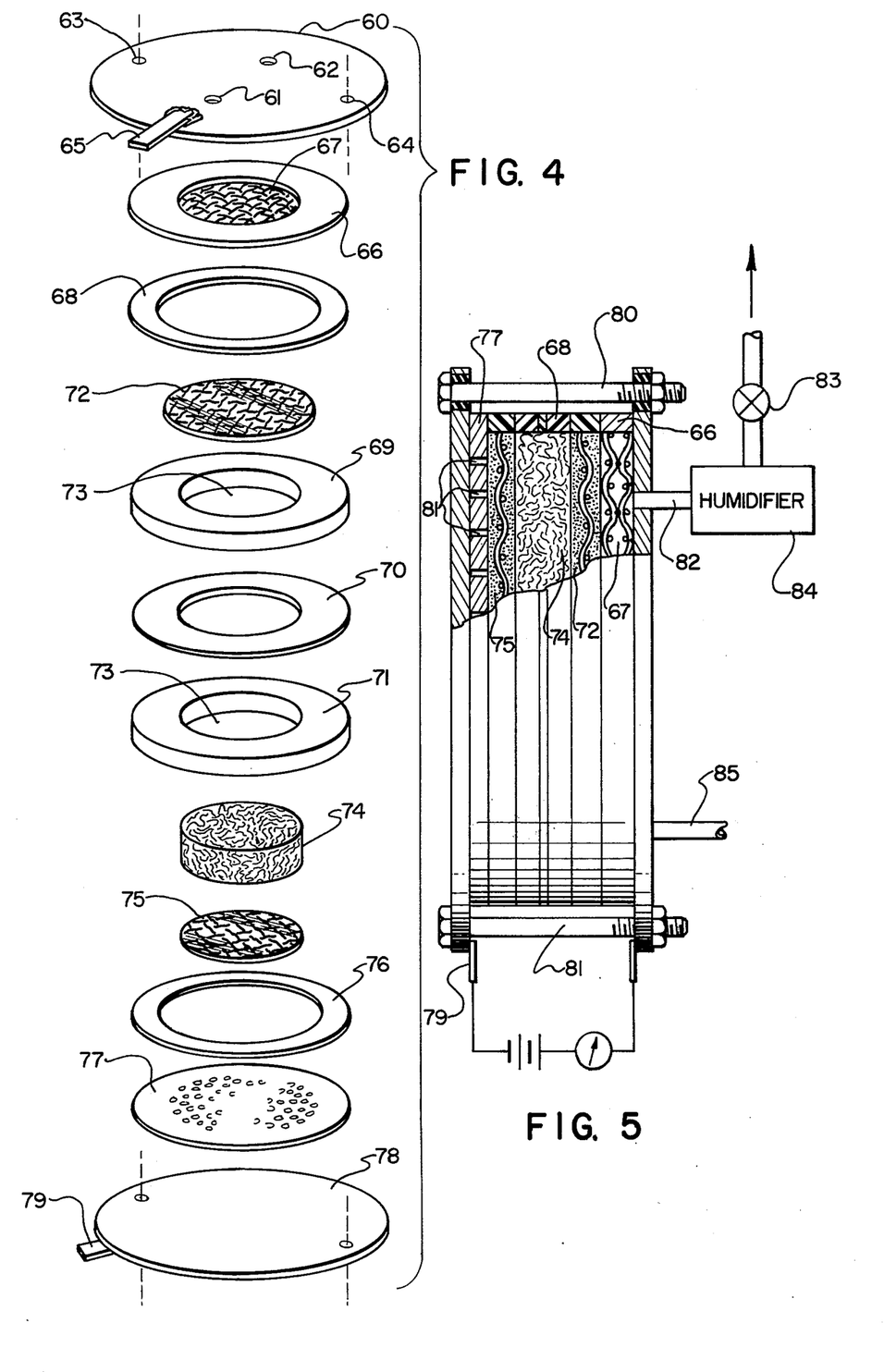
FIG. 4 is an exploded perspective view of an alternative cell construction utilizing an aqueous electrolyte sorbed in a suitable matrix.
FIG. 5 is a partially broken wave view of the cell of FIG. 4 in the assembled state.

In the gas detecting assembly illustrated in FIGS. 2 and 3, a solid polymer electrolyte is utilized as the medium for transporting hydrogen ions from the sensing electrode to the counter/reference electrode. In the alternative constructions illustrated in FIGS. 4 and 5, a similar assembly is illustrted utilizing a liquid electrolyte immobilized in a glass fiber matrix which is positioned in a suitable chamber. Catalytic, gas permeable, electrodes are positioned at opposite ends of the chamber to provide contact with the electrolyte and to seal the electrolyte in the chamber. As illustrated in FIG. 4 which is an exploded perspective view of the assembly, a titanium endplate 60 is shown at the top having inlet and outlet ports 61 and 62 as well as a suitable bolt holes 63 and 64 which together with a pair of bolts, not shown, hold the assembly together. Titanium endplate 60 functions both as a clamping member for the cell as well as a bipolar current collector having a suitable tb 65 welded or otherwise fastened thereto to allow current flow from the cell. A niobium ring collector 66 having a plurality of expanded tantalum screens 67 welded to the underside thereof is positioned beneath and adjacent to the endplate and provides a means for distributing the gaseous constituent entering the sensing chamber to distribute the gas evenly over the surface of the sensing electrode. A sealing gasket 68 covered with adhesives on both surfaces and preferably made of "Teflon" is positioned between the niobium ring collector and a first polysulfone ring 69 which together with gasket 70 and a second polysulfone ring 71 forms a chamber 73 in which the immobilized liquid electrolyte such as 37% solution of H$_3$PO$_4$ is positioned. A gas permeable, hydrophobic catalytic sensing electrode 72 is positioned adjacent to one end of the polysulfone ring 69 and together with gasket 68 seals the electrolyte containing chamber at one end. Electrode 72 is the electrode at which the incoming gaseous constituents are electrochemically oxidized for detecting purposes. The electrode consists of a current collecting screen member having a bonded mixture of a catalyst and hydrophobic gas permeable particles. The catalyst consists of reduced platinum, 55 iridium alloy particle bonded with hydrophobic particles such as polytetraflourethylene. The electrode is therefore gas permeable, while at the same time, being hydrophobic in nature. The sensing electrode may be formed in the same way as the sensing electrode described in connection with FIG. 2.

The interior chamber 73 formed by the combination of polysulfone rings 69 and 71 and gasket 70receive a fiberglas matrix 74 impregnated with an H$_3$PO$_4$ electrolyte. A second electrode 75 is positioned on the other side of the polysulfone ring 71 to seal chamber 73 at its other end and to provide the counter/reference electrode for the cell. A "Teflon" gasket 76 is positioned between the lower end of the chamber and the hydrogen storing perforated palladium foil 77 which is, in turn, positioned adjacent to a lower endplate 78. The lower endplate 78 has a current collecting tab 79 welded or otherwise fastened thereto to allow the durrent flow through the endplate, the palladium foil and the counter/reference electrode 75.

As may be seen more clearly in FIG. 5, which shows the cell in the assembled position, the two endplates 60 and 78 and the intermediate elements are assembled by means of insulated bolts 80 and 81 to form a cell having a glass matrix element 74 mounted in the polysulfone rings to establish a sensing chamber on the right hand side and a hydrogen chamber on the left hand side. Sensing electrode 72 together with gasket 68 seals the chamber at one end while the counter/reference electrode 75 in conjunction with gasket 76 seals the electrolyte chamber on the other end. The gas sensing chamber includes the gas distribution screen elements 67 and a niobium collector ring. The gas is brought into the chamber by means of an inlet conduit 82, a pump 83 and a humidifier 84. The gas is removed from the chamber through an outlet conduit 85. The gas distribution screens 67 are spot welded together and to the endplate 60 to provide a continuous current path between the sensing electrode and the endplate so that the endplates and their associated tabs 65 and 79 provide a path for current flow through a measuring instrument 86. The cell illustrated in FIG. 5 is similar to the one shown in FIG. 3 in that a perforated foil 77 is positioned adjacent to the counter reference electrode to provide a storage means for the hydrogen produced at the counter/reference electrode by the recombination of the hydrogen ions and electrode. The foil again is of a material which has a high hydrogen solubility such as palladium or a similar material such as Ti-Pd, for example. In addition to the high solubility of the intrinsic material, the foil has perforations or holes, such as illustrated at 87 to increase the surface area of the foil and hence the amount of hydrogen that can be stored in this element. Again, this produces a substantially constant hydrogen partial pressure at the counter/reference electrode to isure constant potential of 0.0 volts at the reference electrode.

EXAMPLE 1

In order to determine the effectiveness of the sensor for detecting a gas such as carbon monoxide, for example, a cell utilizing an immobilized H$_3$PO$_4$ electrolyte in a fiberglass matrix, as shown in FIG. 4 and 5 of the drawings, was constructed using a platinum-5% Ir sensing electrode catalyst and a voltage source of 1.35 volts vs. the Pt/H$_2$ reference electrode. The cell was tested with four gas compositions having a known carbon monoxide concentration. The gases had the following composition:

| Gas | CO(PPM) | Propane (PPM) | CO$_2$(%) | N$_2$ |
| --- | --- | --- | --- | --- |
| 1 | 546 | 68 | 1.95 | Balance |
| 2 | 1100 | 163 | 3.93 | " |
| 3 | 2050 | 377 | 5.83 | " |
| 4 | 5230 | 870 | 8.07 | " |

As can be seen, the test gases contain no air (O$_2$) so the samples are diluted with air. A dilution factor of approximately 18.2 was utilized and a feel flow of approximately 106 cc/min was utilized. the sample was saturated by passing through a water saturator, the gas detecting cell was stabilized for a period of 1 hour to stabilize the background readings and a background of approximately 24 microamps was noted and was subtracted from the reading. The following readings were obtained:

| Gas | Conc. CO(PPM) | Dilution Factor | Sensing Conc. (PPM) | Reading ($\mu A$) |
|---|---|---|---|---|
| 1 | 546 | 18.2 | 30 | 18 |
| 2 | 1100 | " | 60.5 | 39 |
| 3 | 2050 | " | 110 | 68 |
| 4 | 5230 | " | 288 | 165 |

Figure 6:
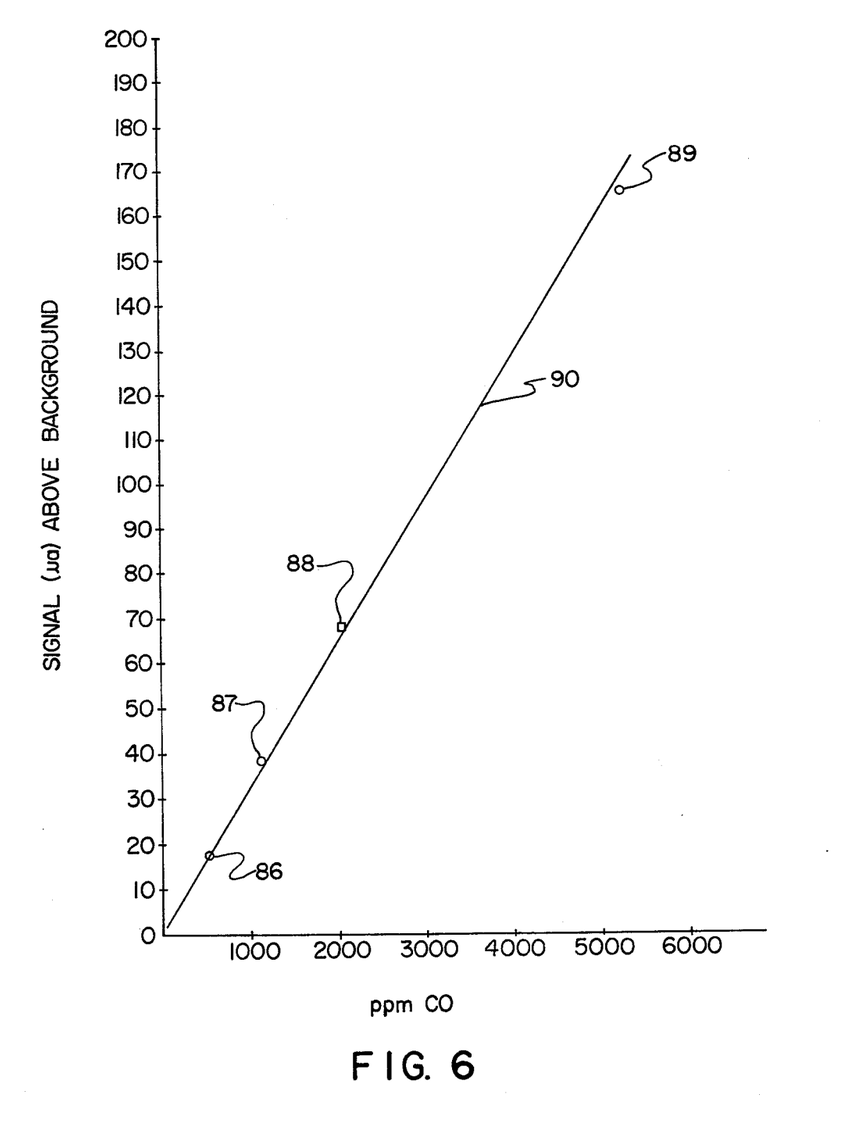
FIG. 6 is a graphic representation of the response curve of a cell for detecting carbon monoxide.

FIG. 6 illustrates graphically the relationship of carbon monoxide concentration and the output current readings from the cell. In the graph of FIG. 6 the output current reading are plotted in microamperes along the ordinate and the gas concentration along the abscissa. The test points 86, 87, 88 and 89 permit the drawing of a linear responsive curve 90 which indicates that the instrument response to carbon monoxide is linear and for the particular instrument show a response to roughly 30 parts per million of carbon monoxide per microamp. Furthermore, this particular cell was linear over a range of 0 to 5000 parts per million thus providing a simple, accurte gas sensing cell over a fairly wide range of gas concentrations.

EXAMPLE 2

A gas sensor identical in construction to the one in Example 1 was used to detect Nitric Oxide (NO) in a nitrogen carrier. The NO was suitably diluted in nitrogen ($N_2$) to obtain the following concentrations of NO and the background current at 0 concentration was 50 $\mu$ amps.

| Gas | No Concen. (PPM) | Reading (Micro A.) |
|---|---|---|
| 1 | 5 | 70 |
| 2 | 13 | 100 |
| 3 | 31 | 200 |
| 4 | 73 | 370 |
| 5 | 120 | 590 |
| 6 | 200 | 940 |

When this data is plotted graphically, a linear response curve can be drawn for this data which shows a response of approximately 4–5 microamps per part per million of Nitric Oxide.

EXAMPLE 3

A gas sensor such as the one described in Example 1 was prepared with one change. The sensing electrode was made of pure graphite rather than Pt-5% Ir and was used to detect Nitric Oxide (NO). The Nitric Oxide was suitably diluted in nitrogen ($N_2$) to obtain the following known concentrations. The background current at 0 parts per million of NO was 50$\mu$ amps.

| Gas | No Concen. (PPM) | Reading (Micro A.) |
|---|---|---|
| 1 | 10 | 80 |
| 2 | 32 | 160 |
| 3 | 78 | 340 |
| 4 | 130 | 520 |
| 5 | 190 | 770 |

When this data is plotted graphically, a linear response curve can be drawn for this data which shows a response of 3,8$\mu$ amps/PPM of NO. The graphite electrode is thus less active for NO sensing than a Pt-5% Ir electrode but may be less sensitive to the presence of CO.

EXAMPLE 4

A cell similar to that described in Example 1 was constructed. Alcohol in known concentrations were tested in a range equivalent to 0.5 to 0.15 per cent blood alcohol. This range is, of course, the crucial range for determination of intoxication. The following results were obtained:

| Gas | Conc. (PPM) | Reading (Micro A.) |
|---|---|---|
| Alcohol Vapor | 2000 (equiv. to 0.05 % blood conc.) | 1.19 (Avg of 2 readings) |
| " | 4000 (equiv to 0.1 % blood conc.) | 2.13 (Avg of 3 readings) |
| " | 6000 (equiv to 0.15 % blood conc.) | 2.93 (Avg of 3 readings) |

It will be obvious from the foregoing that a gas detecting electrochemical cell has been provided which is capableof detecting selective constituents in an incoming gas stream quite accurately and quite effectively. The system is stable and not subject to the type of errors due to variations in the potential at the counter/reference electrode by virtue of a novel sealed chamber electrode configuration in which a hydrogen storing element is provide adjacent to the counter/reference electrode which absorbs and stores molecular hydrogen formed at the electrode to provide a very stable counter/reference electrode.

While a particular embodiment of this invention has been shown, it will, of course, be understood that the invention is not limited thereto since many other modifications both in the circuit arrangement and in the instrumentalities employed may be made. It is contemplated by the appended claims to cover any such modifications that fall within the true scope and spirit of this invention.

What is new and desired to be secured by Letters patent of the United States is:

1. An electrochemical gas detector comprising an ion transporting electrolyte means, a catalytic sensing electrode positioned on one side of said electrolyte means, a counter/reference catalytic electrode positioned on the other side of said electrolyte means, means for applying a voltage between said electrodes to maintain the potential at said sensing electrode equal to or in excess of the potential required to oxidize the gaseous constituent to be detected, means for exposing the sensing electrode to the gaseous constituent to be detected to oxidize said constituent and produce hydrogen ions at said sensor electrode for transport across said electrolyte to said counter/reference electrode to produce molecular hydrogen there, means to maintain a constant reference potential at said counter/reference electrode including means to store the molecular hydrogen produced at said counter/reference electrode to maintain a substantially constant hydrogen partial pressure and a constant reference potential at said counter/reference electrode.

2. The electrochemical gas detector of claim 1 wherein said means to store said molecular hydrogen comprises a foil of metal in which hydrogen is soluble.

3. The electrochemical gas detector according to claim 2 wherein said foil has a plurality of perforations for increasing the surface area of said foil and the amount of hydrogen stored therein.

4. The electrochemical cell of claim 1 wherein said means to store said molecular hydrogen comprises a palladium foil in which hydrogen is soluble.

5. The electrochemical gas detector according to claim 4 wherein said means to store said molecular hydrogen comprises a perforated palladium foil positioned adjacent to said counter/reference electrode.

6. The electrochemical gas detector according to claim 1 wherein said counter/reference electrode and said means to store said molecular hydrogen are positioned in a sealed chamber whereby the molecular hydrogen produced at said counter/reference electrode is the sole source of hydrogen for said reference electrode.

7. The electrochemical gas detector according to claim 6 wherein a perforated palladium foil is positioned adjacent to said counter/reference electrode on said sealed chamber and stores hydrogen to maintain the hydrogen pressure and fthe reference electrode potential substantially constant.

8. The electrochemical gas detector according to claim 1 wherein said ion transportion electrolyte means comprises a solid polymer electrolyte ion exchange membrane.

9. Electrochemical gas detector according to claim 1 wherein said ion transporting electrolyte means comprises an aqueous electrolyte in a matrix.

* * * * *